United States Patent
Bracher et al.

(10) Patent No.: US 7,201,056 B2
(45) Date of Patent: Apr. 10, 2007

(54) DEVICE AND METHOD FOR MEASURING AN EXTRUDED FLAT-CABLE CONDUCTOR

(75) Inventors: Erhard Bracher, Biel (CH); Frédéric Guerne, Courtelary (CH)

(73) Assignee: Zumbach Electronic AG, Orpund (CH)

( * ) Notice: Subject to any disclaimer, the term of this patent is extended or adjusted under 35 U.S.C. 154(b) by 189 days.

(21) Appl. No.: 10/820,746

(22) Filed: Apr. 9, 2004

(65) Prior Publication Data

US 2004/0200285 A1    Oct. 14, 2004

(30) Foreign Application Priority Data

Apr. 10, 2003    (EP) .................................. 03008376

(51) Int. Cl.
*G01N 29/04*    (2006.01)
(52) U.S. Cl. .......................................... 73/624; 73/159
(58) Field of Classification Search ...................... None
See application file for complete search history.

(56) References Cited

U.S. PATENT DOCUMENTS

| | | | |
|---|---|---|---|
| 3,332,279 A | * | 7/1967 | Tompos et al. ................. 73/73 |
| 3,910,104 A | * | 10/1975 | Davies ......................... 73/641 |
| 4,258,573 A | * | 3/1981 | Fontaine ....................... 73/621 |
| 4,375,167 A | * | 3/1983 | Nusbickel et al. ............. 73/644 |
| 4,893,510 A | * | 1/1990 | Ichikawa et al. .............. 73/620 |
| 5,974,885 A | | 11/1999 | Parthasarathi et al. |
| 6,138,515 A | | 10/2000 | Moufle et al. |
| 6,266,983 B1 | * | 7/2001 | Takada et al. ................ 72/11.1 |

FOREIGN PATENT DOCUMENTS

EP        0 831 324 A2     3/1998
WO       WO 01/96853 A1   12/2001

* cited by examiner

*Primary Examiner*—Hezron Williams
*Assistant Examiner*—Rose M. Miller
(74) *Attorney, Agent, or Firm*—Venable LLP; Robert Kinberg; Steven J. Schwarz

(57) ABSTRACT

Provided is a device for measuring at least one parameter of an extruded flat conductor cable in a water bath that follows the extruder. The device distinguishes itself in that the flat conductor cable is guided with one of its flat sides essentially perpendicular across an ultrasonic head arranged in a water bath and that the ultrasonic head is a displaceable ultrasonic head that can be displaced crosswise to the longitudinal direction, or the ultrasonic head is a stationary ultrasonic element row that extends crosswise to the longitudinal direction of the flat conductor cable. This device allows measuring the total width of the flat conductor cable, such that different parameters can be determined.

16 Claims, 7 Drawing Sheets

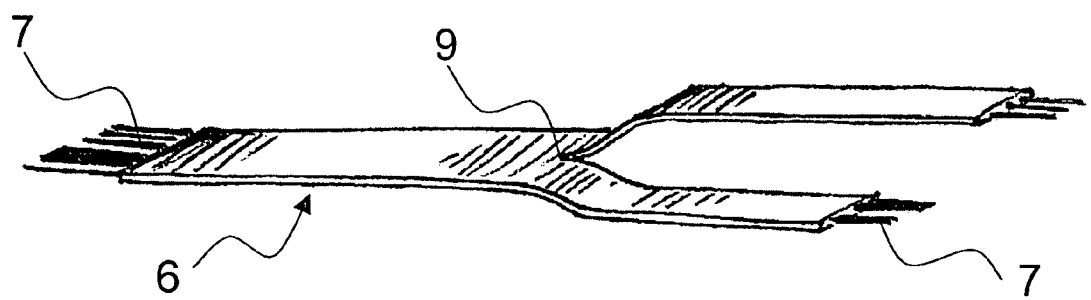
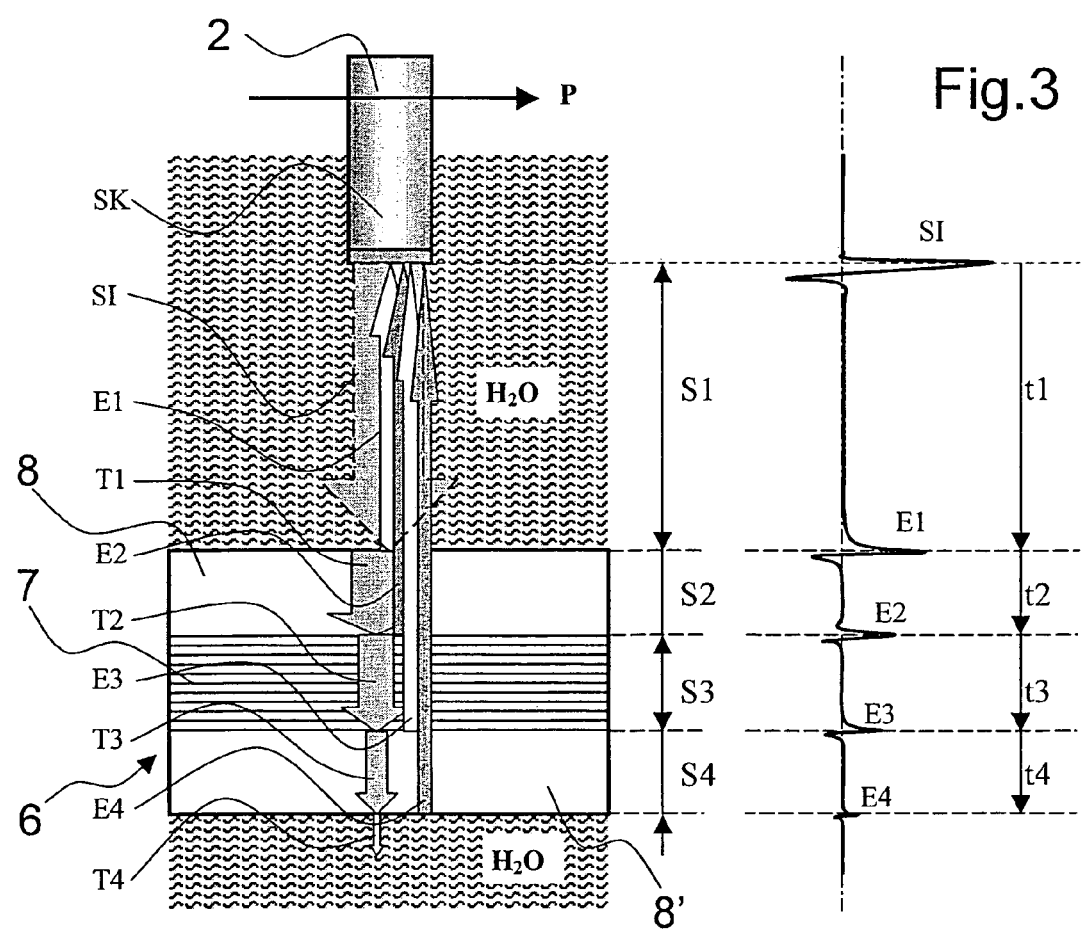

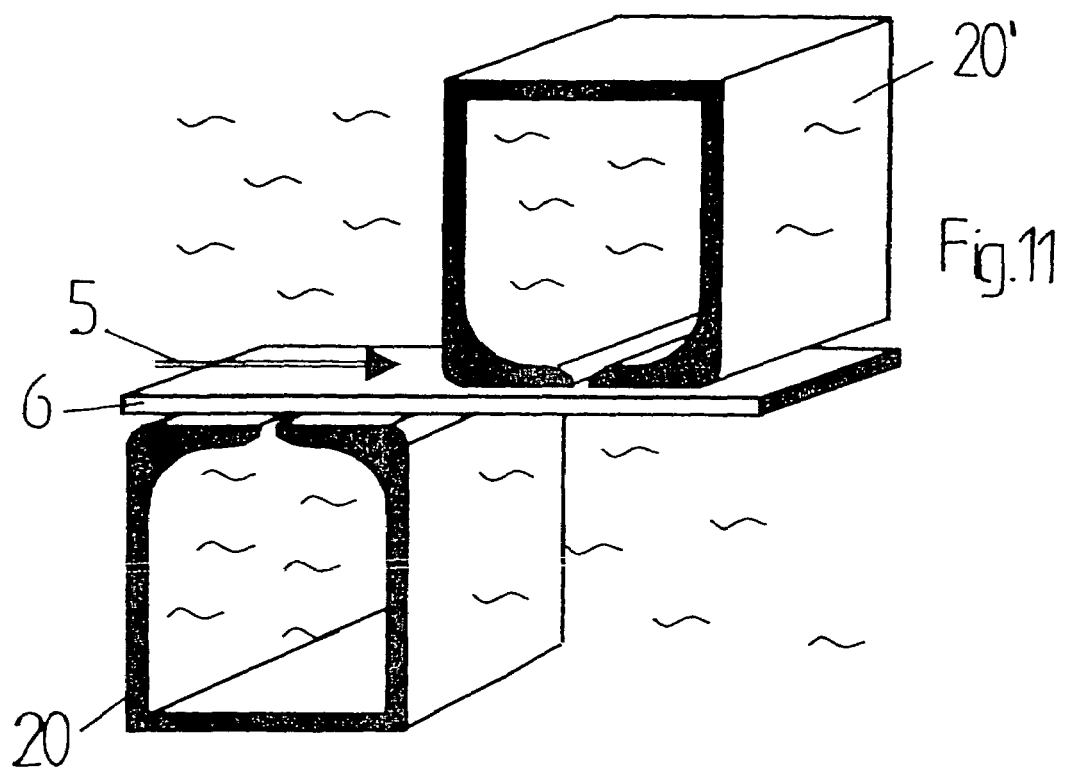
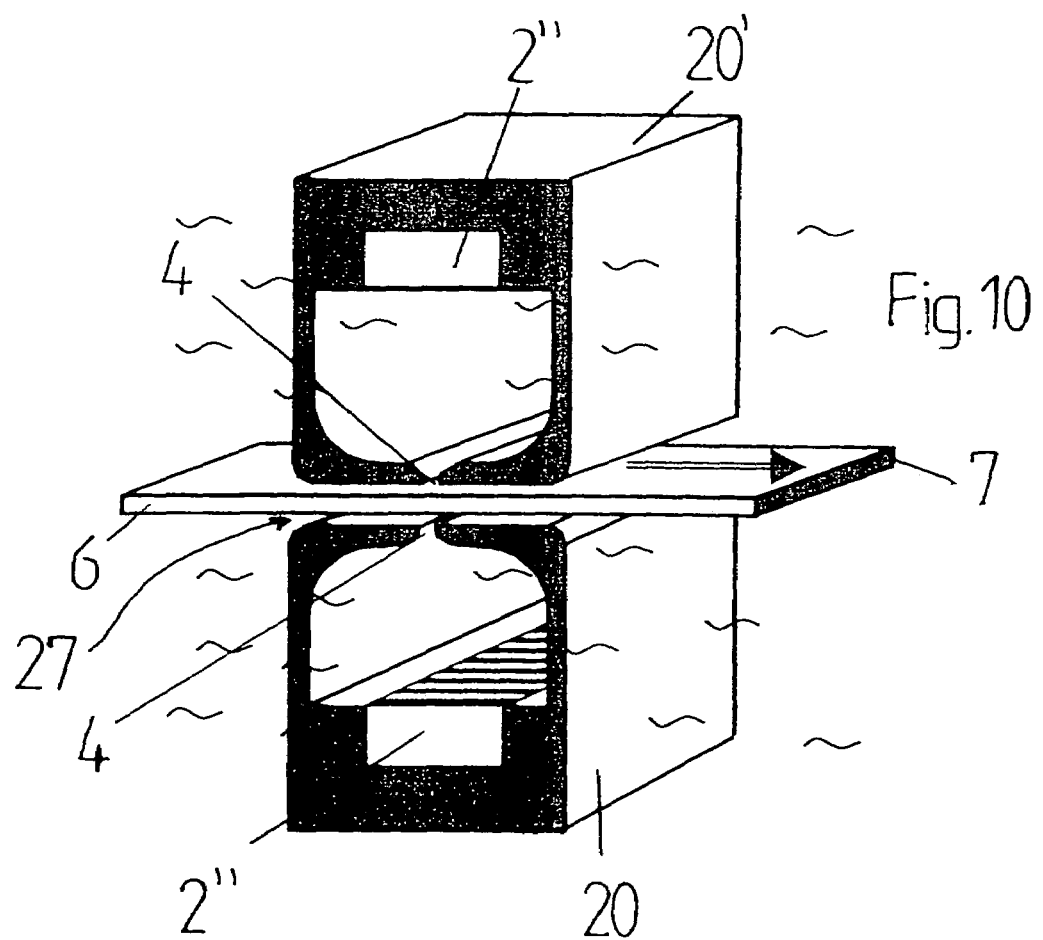

DEVICE AND METHOD FOR MEASURING AN EXTRUDED FLAT-CABLE CONDUCTOR

CROSS-REFERENCE TO RELATED APPLICATION

This application claims the priority of European Patent Application No. 03008376.0, filed on Apr. 10, 2003, the subject matter of which is incorporated herein by reference.

BACKGROUND OF THE INVENTION

The invention relates to a device and a method for measuring at least one parameter of an extruded flat conductor cable in a water bath that follows the extruder.

Numerous devices are already known for measuring and determining cable parameters.

An optical determination of the outside diameter of the cable is possible, for example, or cables can be X-rayed to determine the distribution in transverse direction.

Furthermore known is a method of measuring the wall thickness of insulated strands and to use these data for adjusting the production process. For this, we refer to German reference 25 17 709. A device and a method for testing the wall thickness of an insulated layer is also disclosed in Swiss reference 667327 A5.

A different device for determining the position of a conductor relative to the outside surface of an extruded cable covering is known from reference EP-A 0 612 975.

These known devices use different measuring techniques for determining the desired parameters, wherein the wall thickness, for example, can be determined with the aid of an inductive measurement. However, a measuring technique of this type can be used only for determining the insulation wall thickness. In addition, this type of measurement strongly depends on the conductor dimensions, for example the width and thickness, wherein the sensor must furthermore be in contact with the cable.

The capacitive measuring technique, used multiple times in the past, can be compared to an inductive measuring. The conductors must be grounded for the capacitive measuring.

The ultrasonic technique as well has been used for determining diverse parameters, for example the wall thickness of plates and pipes. The same is true for the insulation of cables, provided they are round cables.

Nowadays, round cables are replaced more and more by flat conductor cables. In particular this applies to the automobile industry where flat conductor cables were produced until now primarily by laminating and/or gluing the insulating layer onto the flat conductors in the cable. However, such flat conductor cables are more and more produced with the aid of extrusion. In the process, problems occur which relate to the precise layout of the flat conductors in the cable, for example with respect to spacing and centricity.

SUMMARY OF THE INVENTION

Thus, it is the object of the present invention to provide a device and a method for determining the desired parameters of an extruded flat conductor cable, for example the insulation wall thickness as well as the positioning and spacing of the individual flat conductors.

This object is solved with the teaching disclosed in the independent claims.

For the device according to the invention, the flat conductor cable (henceforth frequently referred to only as cable) is guided with one of its flat sides essentially in perpendicular direction over at least one ultrasonic head positioned inside a water bath. The water bath preferably is the same one that usually follows the extruder during the extrusion of flat conductor cables and which represents a cooling bath. Owing to the fact that the ultrasonic measuring takes place in a water bath, water as the coupling medium allows contact to be made by the ultrasound to the specimen, a phenomenon that is known.

According to the invention, two alternatives embodiments of the ultrasonic head can be used.

The ultrasonic head for the first alternative is installed in the device in such a way that it can be displaced transverse to the longitudinal direction of the flat conductor cable. For this alternative, several ultrasonic heads can also be used which are all displaceable transverse to the longitudinal direction of the flat conductor cable. The above statement "at least one ultrasonic head" therefore is also valid for one, two, three, four, five . . . many ultrasonic heads.

With the second alternative, the ultrasonic head is a stationary ultrasonic element row that extends transverse to the longitudinal direction of the flat conductor cable. In other words, the ultrasonic head comprises several side-by-side arranged elements which can transmit ultrasonic pulses and, if necessary, also receive ultrasonic echoes, wherein this will be discussed further in the following.

Ultrasonic heads are normally excited with a very short electrical voltage pulse to transmit an ultrasonic pulse. The ultrasonic waves, which impinge on the ultrasonic receiver by way of the contact medium, can be converted to electrical voltages. An ultrasonic head thus can be used as the actual transmitter as well as the receiver. Within the framework of the present documents, a pure ultrasonic transmitter is a device that only transmits an ultrasonic pulse while a receiver is a unit which is used only for converting the ultrasonic waves to electrical voltages.

However, one and the same device can be used as transmitter and receiver. A device of this type is referred to here as ultrasonic converter, wherein such converters can also be called transducers.

For reasons of simplicity, the term "ultrasonic head" in the following refers to a pure ultrasonic transmitter as well as a pure ultrasonic transducer. If there is a reference to a pure ultrasonic transmitter, it means that an ultrasonic receiver is assigned to it on the opposite flat side of the cable. The pure ultrasonic transmitter and the ultrasonic receiver thus form a pair which is displaced along with the ultrasonic head, provided it is displaceable.

Several parameters can be determined as a result of the design of the device according to the invention. These parameters include not only the insulation wall thicknesses, but also the positioning and spacing of the individual flat conductors, as well as the intermediate spaces between these flat conductors. Thus, only one displaceable ultrasonic head or several displaceable heads, for example 2, 3, 4 etc., can be provided.

To be able to precisely determine the exact transverse displacement to the side, and thus also the precise relative position of the ultrasonic head or heads relative to the flat conductor cable to be measured, the side edges and thus the outside contour of the flat conductor cable to be measured should either be known and thus be fixed or should be measured. The position of the flat conductor cable can be determined, for example, by pulling it through a guide, thus determining the position and the outer contour of the cable. The device according to the invention preferably also comprises an additional measuring device for detecting and measuring one side edge of the flat conductor cable. The same is advantageously true for the other side edge, thus making it easy to measure the complete cable width. This measuring device is preferably also an ultrasonic measuring device.

The displaceable ultrasonic head or the displaceable ultrasonic heads is(are) preferably provided with a position sensor which continuously detects the transverse displacement to the side of the ultrasonic head. Thus, the echo signals are continuously detected as function of the relative position of the ultrasonic head relative to the outer contour of the cable.

In the case of a displaceable ultrasonic head, the simplest embodiment of the device according to the invention is provided with only a single displaceable ultrasonic head of this type. However, the ultrasonic head should then be displaceable across the total width of the flat conductor cable so that all desired parameters can be determined.

Of course, it is also possible to use several displaceable ultrasonic heads. In that case, the ultrasonic heads are advantageously offset in longitudinal direction of the flat conductor cable, such that they scan only a specific portion of the total width of the flat conductor cable, for example respectively only half.

The expression "several" ultrasonic heads within the framework of the present documents refers to two, three, four, . . . many ultrasonic heads.

However, it is possible to provide several displaceable ultrasonic heads and arrange these side-by-side, without offset in longitudinal direction. In that case, the ultrasonic heads are preferably displaced simultaneously, but are triggered sequentially, so that the ultrasonic pulses can also be transmitted with a time offset. For example, they can be mounted rigidly on a slide, which can be displaceable as such, thus making the ultrasonic heads displaceable as well. Even a single displaceable ultrasonic head is preferably mounted on such a slide.

If the device according to the invention is provided with several displaceable ultrasonic heads, which can be displaced independent of each other and not jointly, the displacement distance scanned by the ultrasonic head and thus the width of the flat cable conductor can be selected based on the requirements. Two or several ultrasonic heads that are arranged one after another in longitudinal direction can also be provided in that case. The displacement distance can furthermore be selected such that specific regions of the width as well as the complete width of the flat conductor cable are repeatedly scanned and measured. All of this can be configured based on what is desired and required.

A stationary ultrasonic element row can also be used in place of a displaceable ultrasonic head. For this, the width of this ultrasonic element row is dimensioned such that the desired width of the flat conductor cable can be measured. For one embodiment, the ultrasonic element row advantageously extends over the complete width of the flat conductor cable. It is also possible to use two separate stationary ultrasonic element rows which are arranged, for example, offset in longitudinal direction of the flat conductor cable and extend only over a specific region of the flat conductor cable width. The ultrasonic element rows in that case preferably are designed and installed such that the complete width of the flat conductor cable can be scanned and thus measured.

The alternatives discussed herein are based on the joint inventive idea that a flat conductor cable is measured with the aid of at least one ultrasonic head, at least over a specific region of the width and preferably over the complete width.

Based on yet another preferred embodiment, the device according to the invention is provided with a guiding device comprising an interior space. This guiding device is arranged inside the water bath, so that the interior space is also filled with water.

This guiding device is provided with a slot across which the flat conductor cable is guided, such that it makes contact with it or is disposed at a slight distance thereto. A slight distance thereto is understood to mean 0.1–10 mm. This guiding device is arranged such that the slot extends transverse to the longitudinal direction of the flat conductor cable.

The interior space of this guiding device contains an ultrasonic head which transmits ultrasonic waves in the direction of the slot, wherein only the ultrasonic waves that exit through the slot are used for measuring the desired parameters of the flat conductor cable.

The ultrasonic head and/or the ultrasonic transducer used is advantageously provided with a focusing optic that focuses the sound onto a specific point. In that case, the distance is selected such that the focal point is directly on the cable surface.

According to another preferred embodiment the guiding device is essentially closed except for the slot and is provided with a feed opening through which water is forced into the interior space of the guiding device, for example with the aid of a pump. The water pumped into the interior space is pushed out of the slot since this interior space is otherwise closed and thus forms a type of cushion on which the flat conductor cable rests while it is pulled across this slot. The distance between the flat conductor cable and the guiding device can be determined with the aid of this water cushion, for example by adjusting the water-pumping volume. As a result, the precision of the ultrasonic measurement can be improved once more.

The object of the invention is furthermore solved with a method for measuring at least one parameter of an extruded flat conductor cable where the flat conductor cable is measured inside a water bath after it exits an extruder. This method distinguishes itself in that the sound waves transmitted by at least one ultrasonic head impinge essentially perpendicular on at least one of the two flat sides of the flat conductor, and a) the ultrasonic head used can be displaced transverse to the longitudinal direction of the flat conductor cable, or b) a stationary ultrasonic element row is used as ultrasonic head which extends across the width of the flat conductor cable, wherein the parameter or the parameters to be measured is(are) determined with the aid of one or several reflected ultrasonic echoes.

The reflected ultrasonic echo is preferably evaluated as A scan and/or amplitude image and is displayed as a function of the transverse direction of the flat conductor cable. The parameters determined with the aid of the method according to the invention can be used to control the production method.

BRIEF DESCRIPTION OF THE DRAWINGS

In the following, the invention is explained with the aid of the drawings, which show schematic representations of preferred embodiments that are not true to scale. The drawings show in:

FIG. 1 A schematic representation of a flat conductor cable;

FIG. 3 A sectional view of an ultrasonic head and a flat conductor cable with the resulting echo signals;

FIG. 10 A perspective schematic view of a different embodiment with two opposite arranged guiding devices;

FIG. 11 An analog view to FIG. 10, wherein the two guiding devices are arranged offset in longitudinal direction of the flat conductor cable;

DETAILED DESCRIPTION OF THE INVENTION

Figure 2:
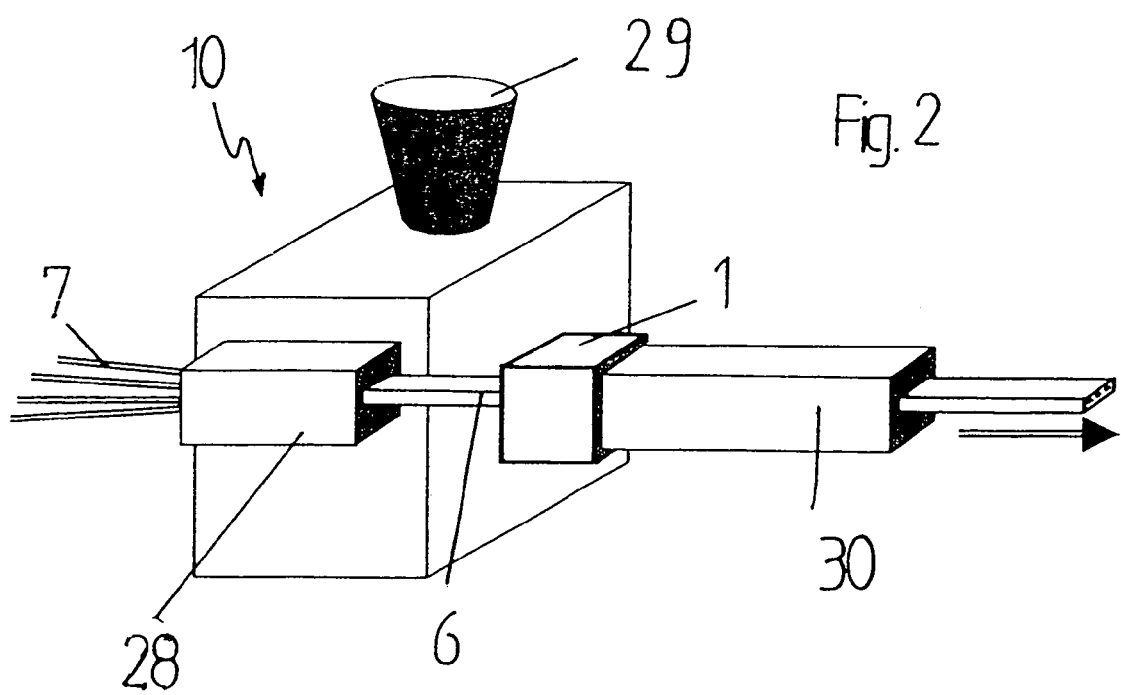
FIG. 2 A schematic representation of an extruder for extruding the flat conductor cable shown in FIG. 1, with integrated device according to the invention.

FIG. 1 shows a perspective view of a standard flat conductor cable 6 with several flat conductors 7, embedded in an insulating plastic layer that is also referred to as insulating layer. The cable 6 is provided with a separating longitudinal cut 9 for dividing the cable into two parts following the production. The extruder 10, shown schematically and in simplified form in FIG. 2, is provided with an extrusion nozzle 28 to which several flat conductors 7 are supplied for producing the cable 6 shown in FIG. 1. These flat conductors 7 are embedded in a plastic material in the extrusion nozzle 28 and are extruded together with this material as flat conductor cable 6. The plastic material is filled into a funnel 29, is heated in the known manner, and is then supplied to the extruder nozzle 28.

Once it leaves the extruder nozzle 28, the cable 6 is guided into a cooling bath 30 where it is cooled with water. The device 1 according to the invention is arranged at the start of the cooling bath 30 and/or the cooling section.

An ultrasonic head 2 is used for measuring the cable 6. FIG. 3 schematically shows the situation where an ultrasonic head 2 is arranged above one of the flat conductors 7 in the flat conductor cable 6. The cable 6 is located in a water bath and is pulled across the ultrasonic head 2. The ultrasonic pulse transmitted by the ultrasonic head 2 travels in the direction of the flat conductor cable 6 and is reflected there at the different boundary surfaces. The first reflection occurs at the boundary surface between the water and the upper external casing surface of the flat conductor cable 6. The first ultrasonic echo E1 formed at this boundary surface returns to the ultrasonic head 2 and is recorded there. The ultrasonic head 2 therefore represents an ultrasonic transducer.

Ultrasonic echoes can be displayed in different ways, for example on an oscillograph or on a computer monitor, as shown on the right side of FIG. 3. The transmitted ultrasonic pulse is shown as SI. The first ultrasonic echo E1 is obtained following the echo transit time t1.

The second ultrasonic echo E2 from the ultrasonic pulse transmitted by the ultrasonic head 3 is generated at the boundary surface between the upper insulation layer 8 and the flat conductor 7. The echo transit time t2 is assigned to this second ultrasonic echo E2.

An additional ultrasonic echo E3 is generated at the boundary surface between the lower boundary layer for the flat conductor 7 and the upper boundary layer for the insulation layer 8' that is arranged underneath. This echo transit time is given the reference t3. The fourth ultrasonic echo E4 is generated at the boundary surface between the lower insulation layer 8' of cable 6 and the water underneath it.

As is known, ultrasonic echoes are generated through reflection at the boundary surfaces where materials with different acoustic impedance meet. For the case at hand, materials of this type are the materials for the insulation layer 8 and the flat conductor 7. Changes or jumps in the acoustic impedance at the boundary surfaces along the propagation direction lead to a partial reflection of the acoustic energy and thus simultaneously to a weakening in propagation direction. The originally transmitted ultrasonic pulse is given the reference SI in FIG. 3. Following the reflection at the first boundary layer and the generating of the ultrasonic echo E1, the original ultrasonic pulse SI is weakened and continues in the weakened form as T1. The same analog behavior applies to the further weakened ultrasonic pulses T2, T3 and T4.

The device according to the invention uses the so-called A-image (amplitude image) for the measuring, which is also referred to as A scan. The chronological progression of the ultrasonic pulses and the back-scattered ultrasonic echoes are measured and evaluated in real time in a signal processor. The results obtained can be displayed in easy-to-read graphic form on a monitor. For this, the echo times which are converted to a dimension are shown on one axis as real distances while the position of the active ultrasonic head is shown on the other axis, that is in transverse direction and relative to the reference edge of the flat conductor cable. In this way, a clearly readable virtual image of the respective cable cross section is generated, wherein this situation is illustrated on the right side of FIG. 3. The vertical position corresponds to the echo transit time (meaning the penetration depth) and the amplitude corresponds to the echo intensity.

Only the most important ultrasonic echoes are explained in FIG. 3 and in the above explanatory text, wherein different echoes such as the bottom echo also exist.

Figure 4:
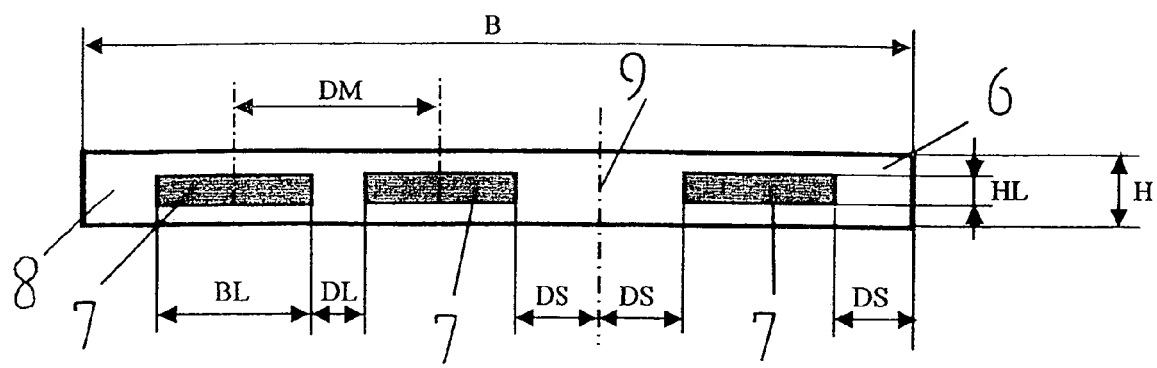
FIG. 4 A schematic cross-sectional view through the flat conductor cable with the parameters which can be determined with the aid of the device according to the invention.

FIG. 4 shows a schematic section through a cable 6. A total of three flat conductors 7 are embedded in the insulation layer 8 for this cable 6. In addition, this cable has a separating cut 9. Various parameters are shown in this Figure which can be measured with the aid of the device and the method according to the invention.

Among other things, these parameters include:
BL—width of the conductor; HL—height of the conductor; DL—distance of the neighboring side edges to two flat conductors 7; DS—distance of the side edge of the outer and/or center flat conductor 7 to the separating cut 9; H=thickness of the flat conductor cable 6; HL—thickness/height of the flat conductor 7 and DM=distance between the longitudinal center lines of two adjacent flat conductors 7.

Figure 5:
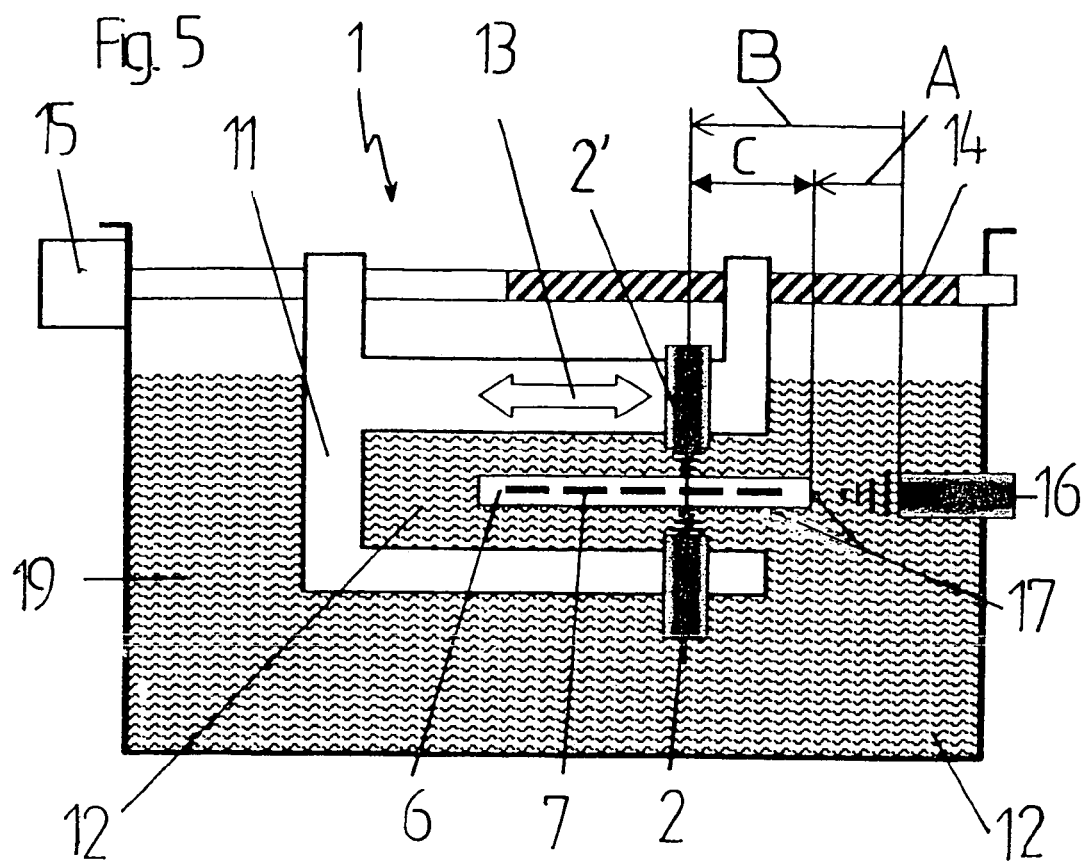
FIG. 5 A schematic cross-sectional view through a water trough with built-in device according to the invention.

FIG. 5 shows a schematic sectional view through a water bath 19 with integrated device 1 according to the invention. The section extends approximately perpendicular to the longitudinal axis of the flat conductor cable 6 to be measured, which is provided with a total of five flat conductors 7. The flat conductor cable 6 is pulled with a slide 11 through an approximately C-shaped recess 12 that is open to the side (shown on the right side in FIG. 5) and is filled with water.

The slide 11 can be moved back and forth transverse to the longitudinal direction of the cable 6 and thus in the direction of double arrow 13. This movement is effected with the aid of a spindle 14 which is driven by the drive 15, for example a direct-current (DC) motor, provided with an encoder for detecting the position of slide 11 and thus also the position of the ultrasonic heads 2, 2' which are explained further in the following. A stepping motor can be used instead, for which the position is clearly determined by the drive. Drive and spindle can also be replaced by a pneumatic cylinder.

The ultrasonic head 2 is arranged below the cable 6 while the ultrasonic head 2' is arranged above the cable 6. The ultrasonic head 2 in this case can be a pure ultrasonic transmitter while the ultrasonic head 2' can be a pure receiver or vice versa. For the embodiment shown, the ultrasonic heads 2, 2' can also be ultrasonic transducers.

An additional measuring device 16 for detecting the position of side edge 17 of cable 6 is installed to the side of the cable 6, wherein this device can also be an ultrasonic head/ultrasonic transducer. The distance A between this measuring device 16 and the side edge 17 of cable 6 can be determined with the aid of this additional measuring device 16.

The complete width of the cable 6 to be measured is scanned and measured during the back and forth movement of slide 11 and thus also the ultrasonic heads 2, 2'. The ultrasonic echoes generated in the process are processed with the aid of a computer, wherein the values for the position detection of slide 11 are also fed to this computer by the additional measuring device 16 and the encoder. From this, the distance B between the ultrasonic head 2, 2' and the additional measuring device 16 is computed by using the values for the distance A. The distance C between the ultrasonic heads 2, 2' and the side edge 17 of the cable 6 follows from this.

Figure 6:
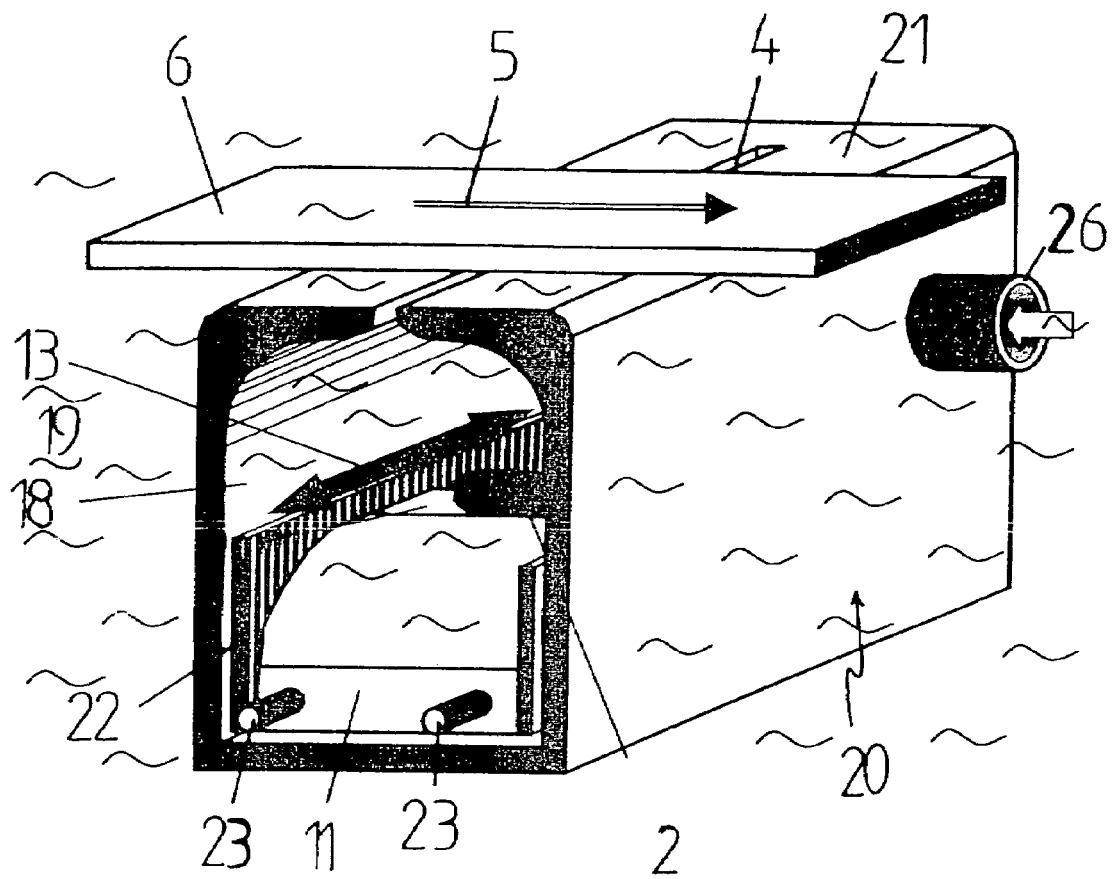
FIG. 6 A perspective view of a guiding device for the device according to the invention, provided with a displaceable ultrasonic head.

According to the perspective view of the device shown in FIG. 6, the slide 11 is moved back and forth in the direction of double arrow 13 inside the interior space 18 of a guiding device 20 that is submerged in the water bath 19. This guiding device 20 is approximately cube-shaped and contains a slot 4 in its upper, horizontal, flat surface 21. The cable 6 is pulled across the slot at 90° to the slot, that it rests approximately on this flat surface 21. The pulling direction and/or the longitudinal direction of cable 6 is shown with arrow 5.

Figure 7:
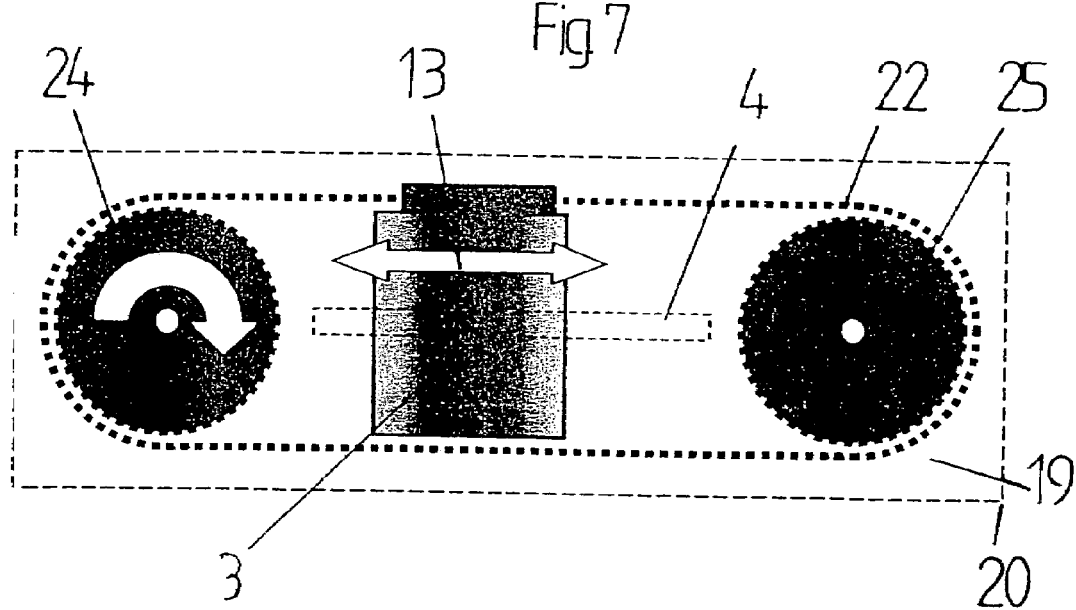
FIG. 7 A functional view from the top of the guiding device shown in FIG. 6.

The slide 11 is guided with the aid of guide rails 23 and is connected to a toothed belt 22 which is moved back and forth with a driven toothed gear 24 (compare FIG. 7). The toothed belt 22 is deflected by a non-driven toothed gear 25.

The slide 11 comprises an ultrasonic head 2 which transmits the ultrasonic pulse in the direction of slot 4. The ultrasonic waves travel through the slot 4, impinge on the cable 6 and are reflected thereon. The reflected ultrasonic echoes again travel through the slot 4 and are received by the ultrasonic head 2. Thus, the ultrasonic head 2 in this case is an ultrasonic transducer.

The guiding device 20 is provided with a pipe section 26 on the side, through which water is forced into the interior space 18 of the guiding device 20 by using a suitable means, for example a pump (not shown herein). This water then flows through the slot 4 out of the interior space 18 and forms on the horizontal upper wall 21 of the guiding device 20 a water cushion or water film along which the cable 6 glides and which fixes the distance between the cable 6 and the surface of the upper horizontal wall 21. By the way, it is not absolutely necessary for the upper wall 21 to be strictly horizontal and/or flat. It can also bulge slightly toward the outside, wherein the slit 4 is then located at the apex of this bulge. On the whole, this results in a yoke-type shape relative to the cross section.

Figure 8:
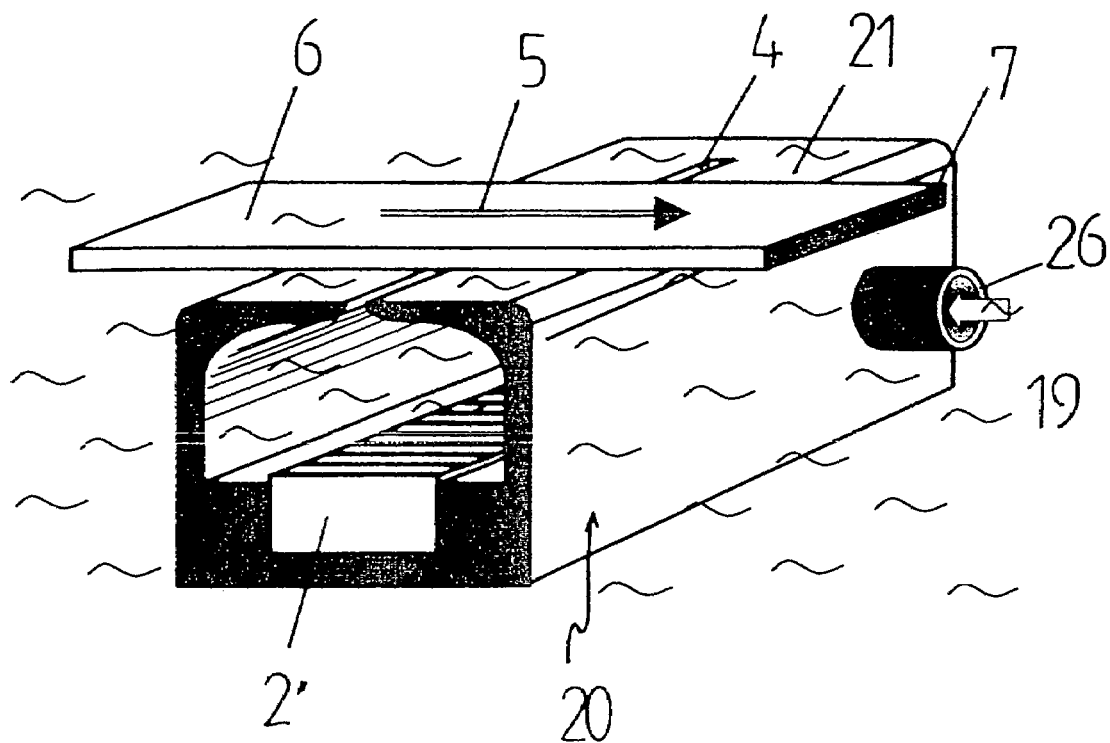
FIG. 8 An analog view to FIG. 6, provided with an ultrasonic head in the form of an ultrasonic element row.
Figure 9:
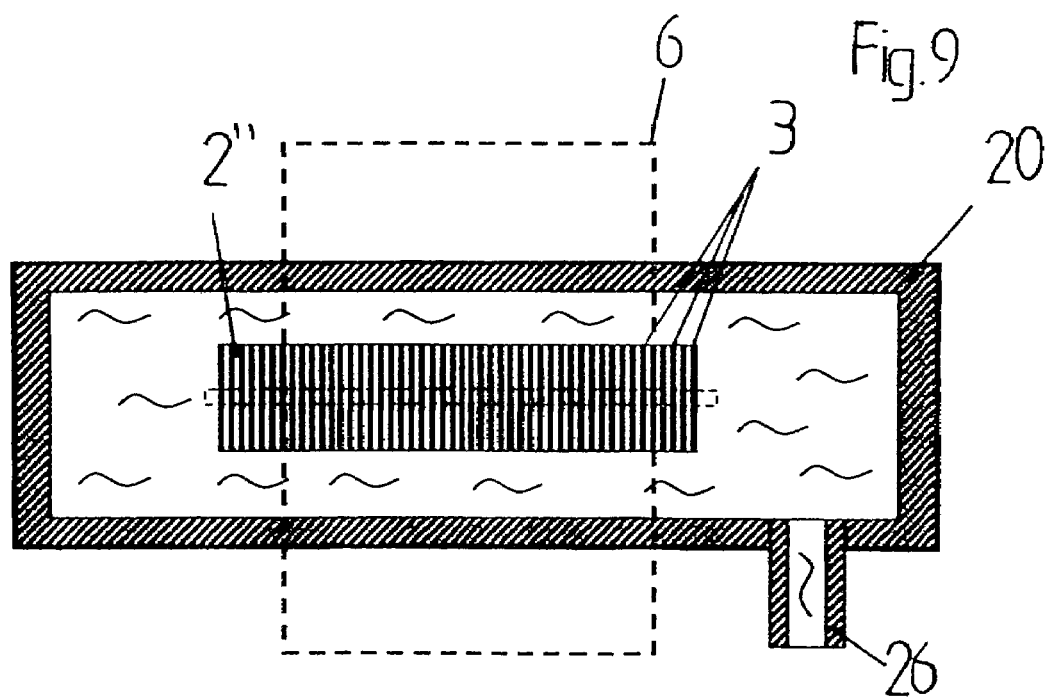
FIG. 9 An analog view to FIG. 7.

The embodiment shown in FIGS. 8 and 9 approximately corresponds to the embodiment shown in FIGS. 6 and 7 with respect to the guiding device 20, wherein identical parts and elements are given the same reference numbers and this applies not only to those two embodiments, but is generally true within the framework of the present invention.

The difference to the embodiment shown in FIG. 6 is that for the embodiment shown in FIGS. 8 and 9, the ultrasonic head is an ultrasonic element row 2", which cannot be displaced but is stationary. This element row is provided with several side-by-side arranged elements 3 which are arranged transverse to the longitudinal direction 5 and transmit ultrasonic pulses.

Unless otherwise indicated, the ultrasonic heads 2, 2' and 2" for the embodiments shown in FIGS. 6 to 9 are ultrasonic transducers which not only transmit an ultrasonic pulse, but also receive the ultrasonic echo. The embodiment shown in FIG. 10, which is very similar to the one shown in FIG. 8, is provided with two guiding devices 20, 20', arranged such that their slots 4, 4' are positioned opposite each other, so that the cable 6 is pulled through the gap 27 that forms between these two guiding devices 20, 20'. Each of these guiding devices 20, 20' is provided with an ultrasonic element row 2". The two ultrasonic element rows 2" in that case can also be transducers. It is furthermore possible that one of the ultrasonic element rows 2" is a pure transmitter and the other one a pure receiver.

The guiding devices 20, 20' need not be arranged opposite each other, but can be arranged such that they are offset in longitudinal direction 5, as shown in FIG. 11. These guiding devices 20, 20' can be provided with a displaceable ultrasonic head as well as with a stationary ultrasonic element row, depending on the requirements.

It is also possible to design the above-described guiding devices 20, 20', provided with a displaceable ultrasonic head 2, 2', such that the guiding devices 20, 20' themselves can be displaced in transverse direction and comprise an ultrasonic head 2, 2' that is positioned stationary therein, thus allowing the ultrasonic heads 2, 2' to be displaced. An embodiment of this type corresponds approximately to the one shown in FIG. 5.

The measuring device 1 according to the invention is arranged so as to follow the extrusion nozzle 28 as closely as possible, so that the measuring results can be made available with minimum delay. These values can then be used for a quick adjustment of the production parameters, for example the wall thickness and centricity of the conductors, wherein this is advantageously done with computer control.

Different parameters of the cable 6 to be measured can be determined with the device 1 according to the invention. For example, echoes can be used to determine the wall thickness if the ultrasonic head is positioned above the flat conductor 7. Furthermore, a suitable analysis of the echo values can be used to determine the conductor width and the conductor spacing when the ultrasonic head moves across the edges of conductor 7, which is explained, for example, in the following with the aid of FIGS. 12 and 13.

Figure 12:
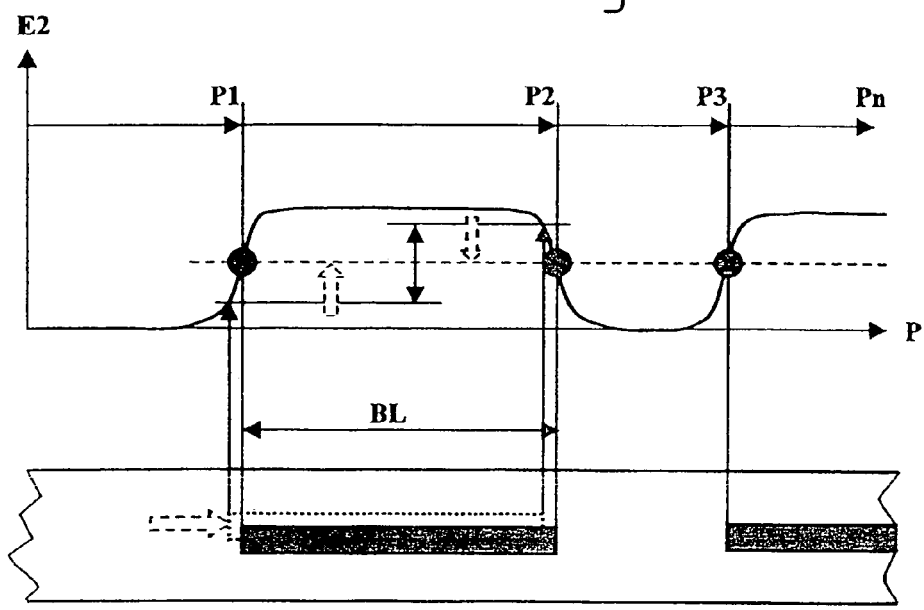
FIG. 12 A diagram of an echo signal, obtained when measuring the flat conductor cable shown schematically underneath.
Figure 13:
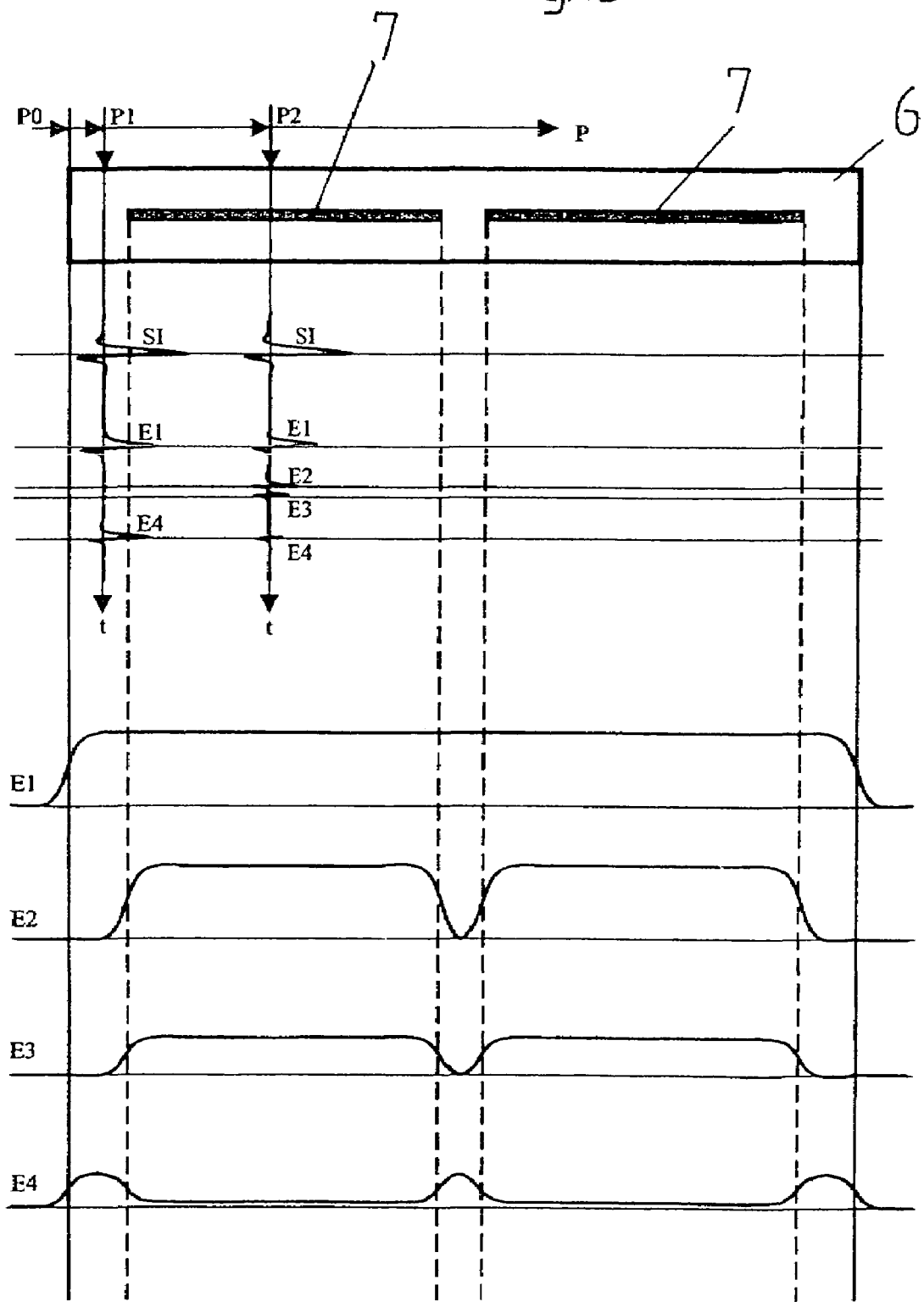
FIG. 13 A diagram showing different echo signals obtained during the measuring of the flat conductor cable shown above.

FIG. 13 shows the amplitude curves for the ultrasonic echoes E1, E2, E3 and E4 for the cable 6 shown at the top of FIG. 13. These ultrasonic echoes E1–E4 have already been described in further detail in the explanations to FIG. 3. Provided the width BL of the flat conductor 7 is known prior to the ultrasonic measuring operation or was measured before the conductors are encased, the trigger points for detecting the edges of the flat conductors 7 can be determined, for example with the aid of the ultrasonic echo E2. This situation is shown in FIG. 12, wherein the known width BL of the flat conductor 7 is centered via the amplitude curve of the ultrasonic echo E2, such that the trigger points determined with the projection (characterized in the Figure by a circle with a cross on the inside) have the same amplitude value.

Assuming that the cable 6 shown in FIG. 12 takes the position shown with dashed line, the cable can be moved far enough to the right as a result of calculations so that the positions P1 and P2 are above the trigger points with the same amplitude. This situation is shown with continuous lines. Once the various trigger points for the flat conductors 7 have been determined in this way, they can be used to calculate the spacing.

The above explanations relate only to a few evaluations that can be made with the aid of the device and method according to the invention.

The invention has been described in detail with respect to exemplary embodiments, and it will now be apparent from the foregoing to those skilled in the art, that changes and modifications may be made without departing from the invention in its broader aspects, and the invention, therefore, as defined in the appended claims, is intended to cover all such changes and modifications that fall within the true spirit of the invention.

What is claimed is:

1. A device for measuring at least one dimension of an extruded flat conductor cable, the device being located in a water bath downstream of an extruder, comprising:
    an ultrasonic head arranged in the water bath such that the flat conductor cable is guided with one of its flat sides essentially perpendicular across the ultrasonic head, the ultrasonic head being adapted to emit sound waves onto at least one side of the flat conductor cable; and
    a measuring device adapted to determine at least one dimension of the flat conductor cable based on at least one sound wave reflected from the flat conductor cable;
    wherein:
        a) the ultrasonic head comprises an ultrasonic head that is displaceable crosswise to the longitudinal direction of the flat conductor cable, or
        b) the ultrasonic head comprises a stationary ultrasonic element row that extends substantially crosswise to the longitudinal direction of the flat conductor cable.

2. The device according to claim 1, wherein the ultrasonic head is an ultrasonic transducer.

3. The device according to claim 1, wherein the ultrasonic head is a pure ultrasonic transmitter and further including an ultrasonic receiver on the opposite flat side of the flat conductor cable operatively associated with the ultrasonic transmitter.

4. The device according to claim 1, wherein the ultrasonic head is an ultrasonic head that is displaceable crosswise to the longitudinal direction of the flat conductor cable, and the ultrasonic head includes a position sensor.

5. The device according to claim 1, wherein the flat conductor cable is guided with its flat side across the ultrasonic head either making contact with it or at a short distance thereto.

6. The device according to claim 1, further comprising an additional measuring device adapted to measure continuously one side edge or both side edges of the flat conductor cable.

7. The device according to claim 1, wherein the ultrasonic head comprises an ultrasonic head that is displaceable crosswise to the longitudinal direction of the flat conductor cable and the ultrasonic head is mounted rigidly on a displaceable slide or arranged inside a displaceable guiding device.

8. A method for measuring at least one dimension of an extruded flat conductor cable by measuring the flat conductor cable in a water bath after it leaves an extruder, comprising:
    emitting sound waves from at least one ultrasonic head substantially perpendicularly onto at least one side of the flat conductor cable; and
    measuring the at least one dimension based on at least one reflected ultrasonic echo; wherein:
        a) the ultrasonic head is displaceable crosswise to the longitudinal direction of the flat conductor cable, or
        b) the ultrasonic head is a stationary ultrasonic element row that extends across the width of the flat conductor cable.

9. The method according to claim 8, further comprising the steps of evaluating the reflected ultrasonic echo as A-scan and/or as amplitude image and displaying the reflected ultrasonic echo as function of the transverse direction of the flat conductor cable.

10. The method according to claim 8, wherein the ultrasonic head is either an ultrasonic transducer or a pure ultrasonic transmitter, and the method further includes providing an ultrasonic sensor operatively associated with the ultrasonic transmitter on the opposite side of the flat conductor cable.

11. The method according to claim 8, wherein the ultrasonic head is displaceable crosswise to the longitudinal direction of the flat conductor cable, the method further comprising:
    displacing the ultrasonic head crosswise to the longitudinal direction of the flat conductor cable during the measuring operation; and
    detecting the position of the ultrasonic head relative to a reference edge of the flat conductor cable.

12. The method according to claim 8, further comprising the step of guiding the flat conductor cable with its flat side across the ultrasonic head, such that the flat side makes contact with the ultrasonic head or is disposed at a short distance to the ultrasonic head.

13. The method according to claim 8, further comprising the steps of:
    providing a guiding device comprising an interior space, and a slot that extends crosswise to the longitudinal direction, wherein the ultrasonic head is located in the interior space;
    guiding the flat conductor cable across the slot such that the flat conductor cable either contacts the slot or is disposed at a short distance to the slot; and
    transmitting ultrasonic waves from the ultrasonic head in the direction of the slot.

14. A device for measuring at least one dimension of an extruded flat conductor cable, the device being located in a water bath downstream of an extruder, comprising:
    an ultrasonic head arranged in the water bath such that the flat conductor cable is guided with one of its flat sides essentially perpendicular across the ultrasonic head, the ultrasonic head being adapted to measure at least one dimension of the extruded flat conductor cable, wherein:
a) the ultrasonic head comprises an ultrasonic head that is displaceable crosswise to the longitudinal direction of the flat conductor cable, or
b) the ultrasonic head comprises a stationary ultrasonic element row that extends substantially crosswise to the longitudinal direction of the flat conductor cable;

the device further comprising a guiding device including an interior space located inside the water bath and filled with water, and a slot that extends crosswise to the longitudinal direction;

wherein the flat conductor cable is guided across the slot so as to make contact or at a short distance thereto, further wherein the ultrasonic head is arranged inside the interior space of the guiding device and transmits the ultrasonic waves in the direction of the slot.

15. The device according to claim 14, wherein the guiding device is essentially closed except for the slot and includes an opening or a pipe section through which water is forceable into the interior space of the guiding device.

16. A device for measuring at least one dimension of an extruded flat conductor cable, the device being located in a water bath downstream of an extruder, comprising:

an ultrasonic head arranged in the water bath such that the flat conductor cable is guided with one of its flat sides essentially perpendicular across the ultrasonic head, the ultrasonic head comprising:

an ultrasonic transducer adapted to emit sound waves onto at least one side of the flat conductor cable and receive sound waves reflected from the at least one flat side;

a pure ultrasonic transmitter adapted to emit sound waves toward the flat conductor cable; and an ultrasonic receiver located on an opposite side of the flat conductor cable from the pure ultrasonic transmitter, and adapted to receive sound waves emitted by the pure ultrasonic transmitter, wherein the ultrasonic transducer receives reflected sound waves at substantially the same time the ultrasonic receiver receives direct sound waves.

* * * * *